(12) United States Patent
Stinnette

(10) Patent No.: US 8,317,845 B2
(45) Date of Patent: Nov. 27, 2012

(54) SCREW AND METHOD OF USE

(75) Inventor: Albert Stinnette, Zephyrhills, FL (US)

(73) Assignee: Alexa Medical, LLC, Zephyrhills, FL (US)

( * ) Notice: Subject to any disclaimer, the term of this patent is extended or adjusted under 35 U.S.C. 154(b) by 1418 days.

(21) Appl. No.: 11/625,275

(22) Filed: Jan. 19, 2007

(65) Prior Publication Data

US 2008/0177334 A1   Jul. 24, 2008

(51) Int. Cl.
*A61B 17/04* (2006.01)
*A61B 17/86* (2006.01)
*A61F 2/08* (2006.01)

(52) U.S. Cl. ......... 606/306; 606/264; 606/265; 606/319

(58) Field of Classification Search ............. 606/264, 606/265, 267, 304, 306, 319, 321, 326–328; 411/388, 396
See application file for complete search history.

(56) References Cited

U.S. PATENT DOCUMENTS

| | | | |
|---|---|---|---|
| 2,489,870 A * | 11/1949 | Dzus ..................... | 606/310 |
| 4,576,608 A | 3/1986 | Homsy | |
| 5,010,145 A | 4/1991 | Ikada et al. | |
| 5,250,049 A | 10/1993 | Michael | |
| 5,443,516 A | 8/1995 | Albrektsson et al. | |
| 5,683,471 A | 11/1997 | Incavo et al. | |
| 5,725,590 A | 3/1998 | Maumy et al. | |
| 5,728,099 A | 3/1998 | Tellman | |
| 5,741,256 A | 4/1998 | Bresina | |
| 5,755,807 A | 5/1998 | Anstaett et al. | |
| 5,759,184 A | 6/1998 | Santangelo | |
| 5,766,174 A | 6/1998 | Perry | |
| 5,766,180 A | 6/1998 | Winquist | |
| 5,779,705 A | 7/1998 | Matthews | |
| 5,853,387 A | 12/1998 | Clegg et al. | |
| 5,855,579 A | 1/1999 | James et al. | |
| 5,871,492 A | 2/1999 | Sorensen | |
| 5,888,204 A | 3/1999 | Ralph et al. | |
| 5,908,422 A | 6/1999 | Bresina | |
| 5,928,231 A | 7/1999 | Klein | |
| 5,973,223 A | 10/1999 | Tellman et al. | |
| 6,004,324 A | 12/1999 | Gahr et al. | |

(Continued)

FOREIGN PATENT DOCUMENTS

EP   1021990 A1   7/2000

(Continued)

OTHER PUBLICATIONS

Blackstone Medical, Inc., Thoracolumbar Systems, downloaded from http://www.blackstonemedical.com/thoracolumbar.php, 1 page.

(Continued)

*Primary Examiner* — Andrew Yang

(74) *Attorney, Agent, or Firm* — Christopher Paradies; Fowler White Boggs P.A.

(57) ABSTRACT

A two-part screw system for use in bone repair and joint replacement includes a first portion and a second portion capable of mating with the first portion. The first portion includes a thread for engaging cancellous bone within a portion of a bone on one side of a fracture. The second portion is coupled to a retention mechanism that couples a portion of the bone on opposite sides of the fracture to a portion of the bone having the first portion of the two-part screw.

15 Claims, 14 Drawing Sheets

U.S. PATENT DOCUMENTS

| | | | |
|---|---|---|---|
| 6,033,407 A | 3/2000 | Behrens | |
| 6,034,295 A | 3/2000 | Rehberg et al. | |
| 6,045,573 A | 4/2000 | Wenstrom, Jr. et al. | |
| 6,056,751 A * | 5/2000 | Fenton, Jr. | 606/28 |
| 6,074,392 A | 6/2000 | Durham | |
| 6,077,264 A | 6/2000 | Chemello | |
| 6,077,265 A | 6/2000 | Werding et al. | |
| 6,123,708 A | 9/2000 | Kilpela et al. | |
| 6,123,711 A * | 9/2000 | Winters | 606/304 |
| 6,143,012 A | 11/2000 | Gausepohl | |
| 6,187,006 B1 | 2/2001 | Keller | |
| 6,187,007 B1 | 2/2001 | Frigg et al. | |
| 6,221,074 B1 | 4/2001 | Cole et al. | |
| 6,228,086 B1 | 5/2001 | Wahl et al. | |
| 6,238,126 B1 | 5/2001 | Dall | |
| 6,261,290 B1 | 7/2001 | Friedl | |
| 6,270,499 B1 | 8/2001 | Leu et al. | |
| 6,277,397 B1 | 8/2001 | Shimizu | |
| 6,302,887 B1 * | 10/2001 | Spranza et al. | 606/916 |
| 6,319,255 B1 | 11/2001 | Grundei et al. | |
| 6,328,764 B1 | 12/2001 | Mady | |
| 6,348,053 B1 | 2/2002 | Cachia | |
| 6,406,477 B1 | 6/2002 | Fujiwara | |
| 6,409,730 B1 | 6/2002 | Green et al. | |
| 6,423,066 B1 | 7/2002 | Harder et al. | |
| 6,448,890 B1 | 9/2002 | Cooper | |
| 6,451,058 B2 | 9/2002 | Tuke et al. | |
| 6,461,360 B1 | 10/2002 | Adam | |
| 6,488,684 B2 | 12/2002 | Bramlet et al. | |
| 6,491,714 B1 | 12/2002 | Bennett | |
| 6,511,481 B2 | 1/2003 | von Hoffmann et al. | |
| 6,517,579 B1 * | 2/2003 | Paulos et al. | 623/13.14 |
| 6,547,791 B1 | 4/2003 | Buehren et al. | |
| 6,558,388 B1 | 5/2003 | Bartsch et al. | |
| 6,569,165 B2 | 5/2003 | Wahl et al. | |
| 6,575,974 B2 | 6/2003 | Gotfried | |
| 6,575,976 B2 | 6/2003 | Grafton | |
| 6,579,294 B2 | 6/2003 | Robioneck | |
| 6,602,293 B1 | 8/2003 | Biermann et al. | |
| 6,632,224 B2 | 10/2003 | Cachia et al. | |
| 6,652,529 B2 | 11/2003 | Swanson | |
| RE38,409 E | 1/2004 | Noiles | |
| 6,702,823 B2 | 3/2004 | Iaia | |
| 6,887,243 B2 | 5/2005 | Culbert | |
| 6,890,333 B2 | 5/2005 | von Hoffmann et al. | |
| 6,908,465 B2 | 6/2005 | von Hoffmann et al. | |
| 6,921,400 B2 | 7/2005 | Sohngen | |
| 6,926,719 B2 | 8/2005 | Sohngen et al. | |
| 7,008,425 B2 | 3/2006 | Phillips | |
| 7,022,348 B2 | 4/2006 | Ketharanathan | |
| 7,070,601 B2 | 7/2006 | Culbert et al. | |
| 2003/0187512 A1 | 10/2003 | Frederick et al. | |
| 2003/0191537 A1 | 10/2003 | Wasielewski | |
| 2003/0229357 A1 | 12/2003 | Dye | |
| 2004/0267360 A1 | 12/2004 | Huber | |
| 2005/0288682 A1 | 12/2005 | Howe | |
| 2006/0149278 A1 | 7/2006 | Abdou | |
| 2006/0155278 A1 | 7/2006 | Warnick | |
| 2007/0004035 A1 | 1/2007 | Sitzmann | |
| 2007/0255420 A1 | 11/2007 | Johnson et al. | |

FOREIGN PATENT DOCUMENTS

| | | |
|---|---|---|
| EP | 1270660 B1 | 12/2004 |
| EP | 1611852 A2 | 1/2006 |
| WO | 9533423 A1 | 12/1995 |
| WO | 9722301 A1 | 6/1997 |
| WO | 2006058221 A2 | 6/2006 |

OTHER PUBLICATIONS

Blackstone Medical, Inc., Cervical Systems, downloaded from http://www.blackstonemedical.com/cervical.php, 1 page.

Stryker, OASYS(trademark) System Overview, Occipito-Cervico-Thoracic System, copyright 2004 Stryker, 8 pages.

Remedica, vol. 4, No. 3, 2006, Advances in Osteoporotic Fracture Management, 39 pages.

Printout of http:///www.ortho.smith-nephew.com/us/Standard.asp?NodeIID=3713, Birmingham Hip Resurfacing System, Smith & Nephew, pp. 1 & 2.

Printout of http://www.zimmer.com/z/ctl/op/global/action/1/id/9223/template/MP/prcat/M2/prod/y, Zimmer Periarticular Plating System, Zimmer, pp. 1-3.

Printout of http://www.zimmer.ccm/z/ctl/op/global/action/1/id/8010/template/MP/prcat/M2/prod/y, Epsilon Durasul Constrained Insert, Zimmer, pp. 1-3.

Zimmer Periarticular Distal Lateral Femoral Locking Plate, Zimmer, printout of http://www.zimmer.com/web/enUS/pdf/product_brochures/234710500_pd_lateral_femoral_lp_ds.pdf, 2 pages.

Printout of http://www.zimmer.com/z/ctl/op/global/action/1/id/9215/template/MP/prcat/M2/prod/y, Zimmer ITST Intertrochantric/Subtrochantric Intramed Nail System, Zimmer, pp. 1 & 2.

Printout of http://www.arthrosurface.com/index.php/content/view/112/76, HemiCAP Resurfacing System, Arthrosurface, pp. 1-4.

Duraloc Constrained Liner, DePuy a Johnson & Johnson company, 4 pages.

Pinnacle A Cetabular Cup System, DePuy a Johnson & Johnson company, pp. 1-44.

Ultamet Metal-on-Metal Articulation, Depuy a Johnson & Johnson company, pp. 1-22.

Hans J Refiar, MD, Preserving the femoral neck in hip replacement: a concept for the future?, Orthopedics Today, p. 4.

Jason Werle, MD, FRCSC et al, The Polyethylene Liner Dissociation in Harris-Galante Acetabular Components, The Journal of Arthroplasty vol. 17. No. 1 2002, pp. 78-81.

Stryker(r) Receives FDA Clearance for LFIT(TM) Anatomic Femoral Heads with X3(R) Liners, Print out of http://biz.yahoo.com/prnews/060826/def010.html?.v=57, 2 pages.

S.J. Caplan, Smith & Nephew Gets a Leg Up, print out of http://biz.yahoo.com/fool/060511/114737837741.html/.v=1, pp. 1 & 2.

Ed Edelson, Experts Predict Hip-Fracture Epidemic, print out of http://news.yahoo.com/s/hsn/20060616/hl_hsn/expertspredicthipfractureepidemic, p. 1 & 2.

Print out of http://www.ortho.smith-nephew.com/us/node.asp?NodeId=3724, Anthology Primary Hip System, Smith & Nephew, 2 pages.

Print out of http://www.ortho.smith-nephew.com/us/node.asp?NodeId=2920, Cobalt Chrome, Smith & Nephew, 1 page.

Print out of http://www.ortho.smith-nephew.com/us/node.asp?NodeId=3761, Oxinium Femoral Heads, Smith & Nephew, 1 page.

Print out of http://www.ortho.smith-nephew.com/us/node.asp?NodeId=2916, Contour Acetabular Rings, Smith & Nephew, 1 page.

Print out of http://www.ortho.smith-nephew.com/us/node.asp?NodeId=2913, Reflection All-Poly, Smith & Nephew, 1 page.

Print out of http://www.ortho.smith-nephew.com/us/node,asp?NodeId=2829, Echelon Revision Hip System, Smith & Nephew, 2 pages.

Print out of http://www.ortho.smith-nephew.com/us/node.asp?NodeId=3727, Emperion Modular Hip System, Smith & Nephew, 2 pages.

Print out of http://www.ortho.smith-nephew.com/us/Standard.asp?NodeId=3708, CPCS Cemented Hip System, Smith & Nephew, 1 page.

Print out of http://www.ortho.smith-nephew.com/us/Standard.asp?NodeId=2897, Echelon HipSystem, Smith & Nephew, 2 pages.

Print out of http://www.ortho.smith-nephew.com/us/Standard.asp?NodeId=3739, Image Porous Hip System, Smith & Nephew, 1 page.

Print out of http://www.ortho.smith-nephew.com/us/Standard.asp?NodeId=3812, Platform Hip System, Smith & Nephew, 2 pages.

Print out of http://www.ortho.smith-nephew.com/us/Standard.asp?NodeId=2867, Spectron Hip System, Smith & Nephew, 2 pages.

Print out of http://www.ortho.smith-nephew.com/us/Standard.asp?NodeId=2868, Synergy Hip System, Smith & Nephew, 2 pages.

Print out of http://www.ortho.smith-nephew.com/us/Standard.asp?NodeId=3728, Accord Cable System, Smith & Nephew, 1 page.

Print out of http://www.ortho.smith-nephew.com/us/Standard.asp?NodeId=3201, Echelon Revision Cemented, Smith & Nephew, 1 page.

Print out of http://www.ortho.smith-nephew.com/us/Standard.asp?NodeId=3096, Spectron Hip System, Smith & Nephew, 1 page.

Print out of http://www.ortho.smith-nephew.com/us/Standard.asp?NodeId=2911, Impaction Grafting, Smith & Nephew, 1 page.

Print out of http://www.ortho.smith-nephew.com/us/Standard.asp?NodeId=3027, Acetabular Options, Smith & Nephew, 1 page.

Print out of http://www.arthrosurface.com/learnHemiCap.html, HemiCAP Resurfacing System, pp. 1-4.

Printout of http://www.orthosmith-nephew.com/us/Standard.asp?NodeID=3006, Trigen Tan Nail, Smith & Nephew, 2 pages.

Printout of http://www.jnjgateway.com/home.jhtml?loc-USENG&page=viewcontent&contendId=0900 . . . , Milagro Interference Screw, Johnson & Johnson, 2 pages.

Printout of http://www.encoremed.com/products/spine/index.htm, Vari Grip fixation product, Encore Medical Corporation, 2 pages.

Printout of http://www.encoremed.com/products/cyclone/index.htm, Cyclone anterior cervical plate, Encore Medical Corporation, 2 pages.

Trochanteric Reattachment Device, Technique Guide by Synthes, 10 pages.

Gamma3, The Compact Version of the Gamma Nail System, Operative Techniquie, Hip Fracture System, Trochanteric and Long Nails, 1 page.

Classic ACP—Exactech,Inc., Anterior Cervical Plate System, downloaded from http://www.exac.com/products/spine/classic-acp on Nov. 13, 2009, 1 page.

* cited by examiner

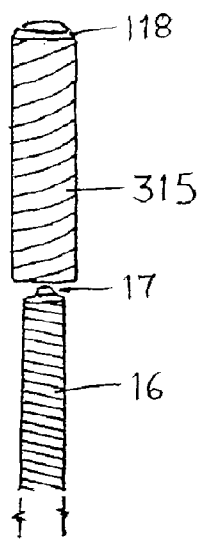
FIG. 3
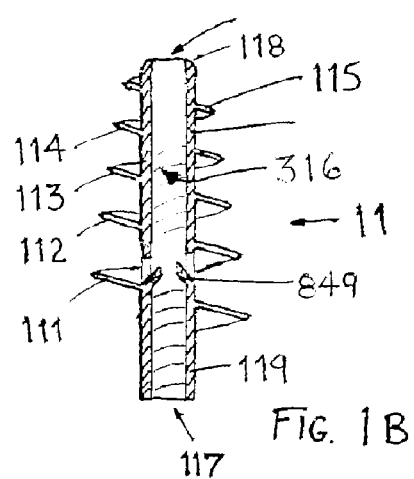
FIG. 1B
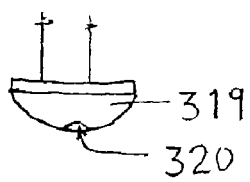
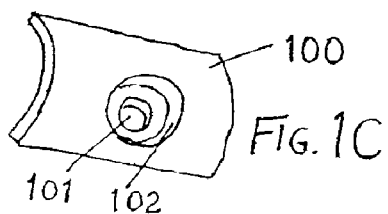
FIG. 1C
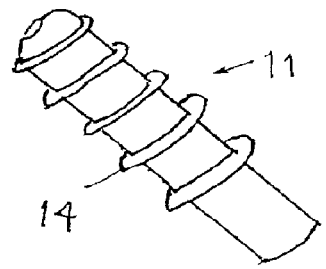
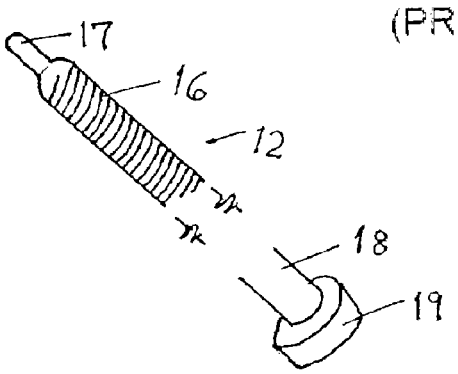
FIG. 1D
(PRIOR ART)
FIG. 1A

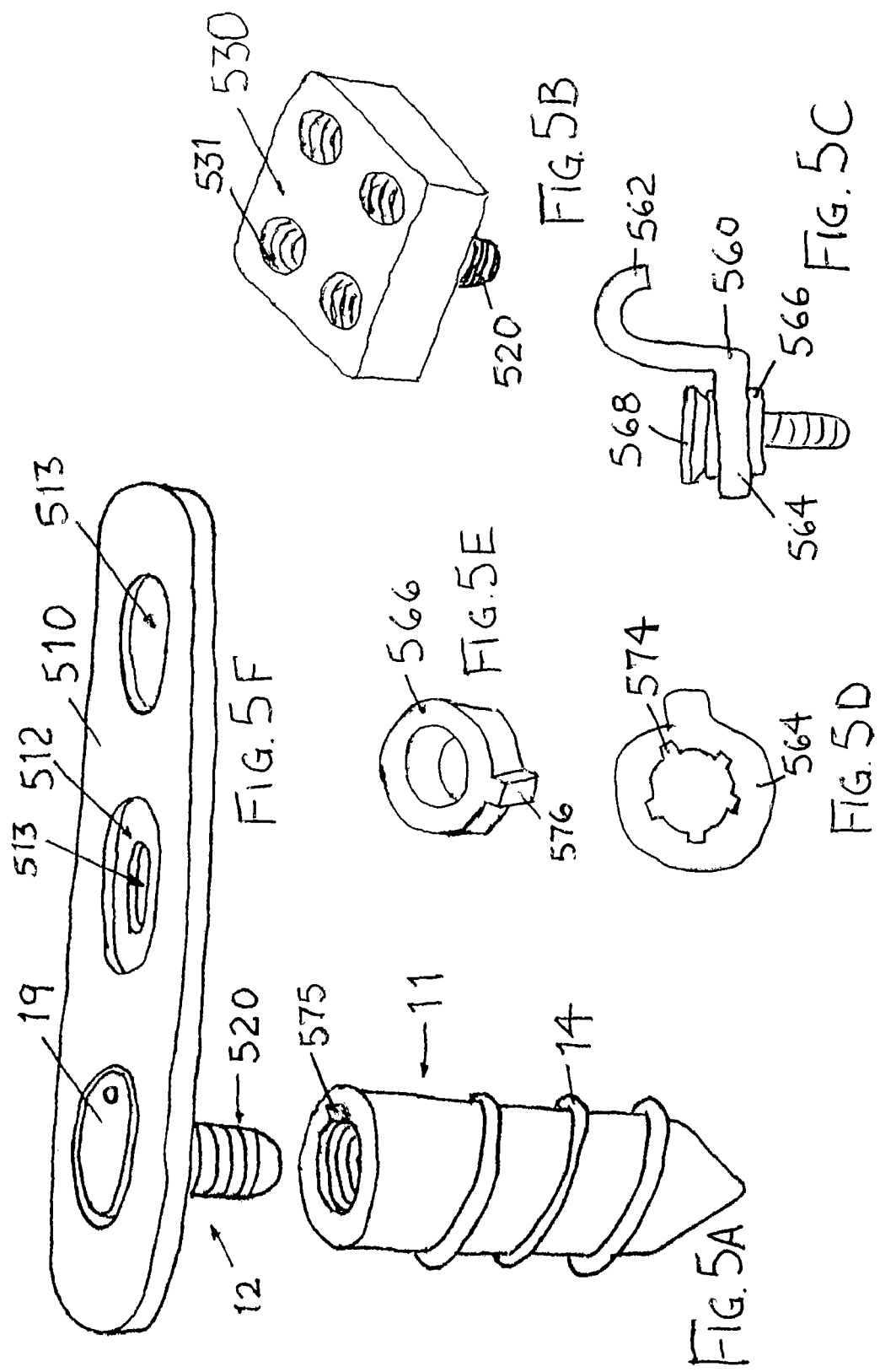

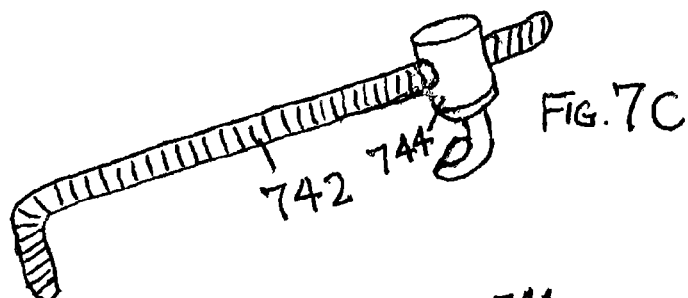
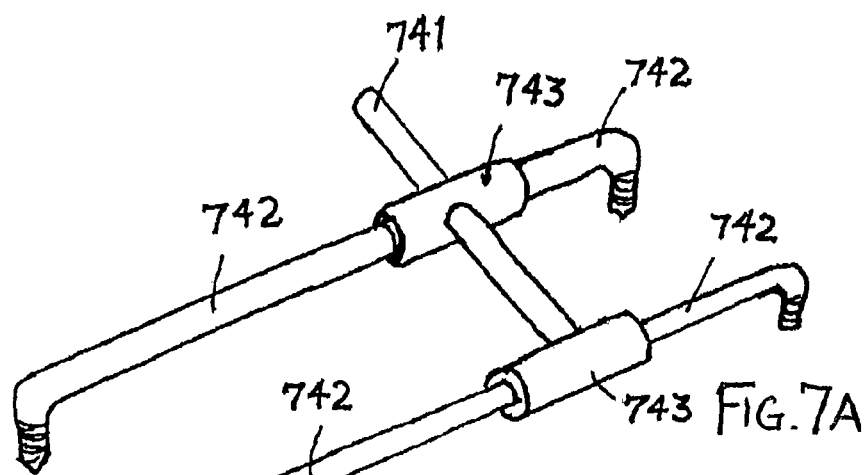
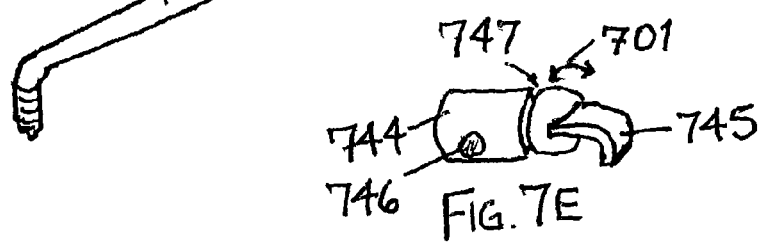
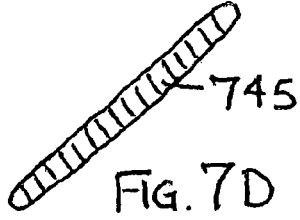
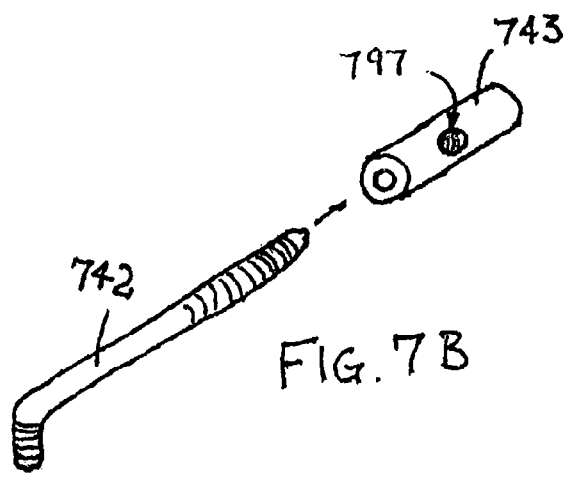

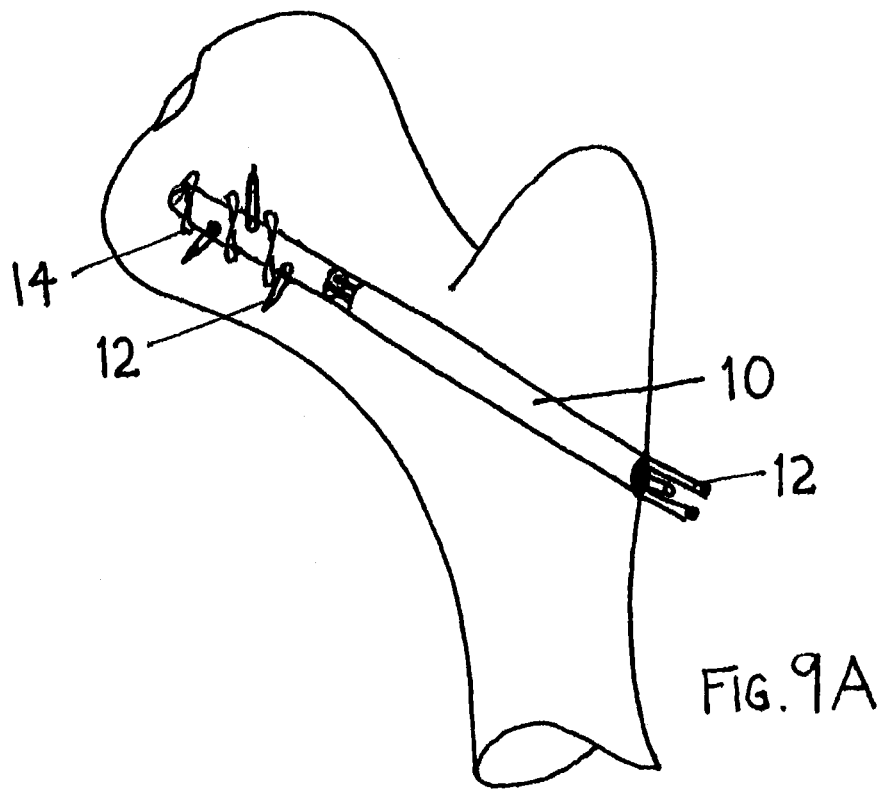
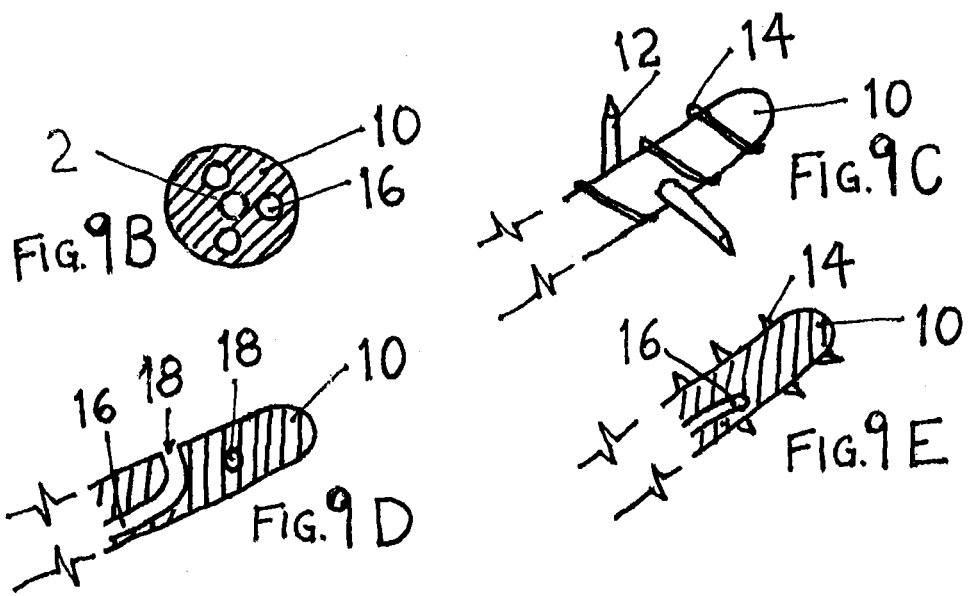

SCREW AND METHOD OF USE

FIELD OF THE INVENTION

The field relates to orthopedics and repair of fractures and wear to load bearing bones and joints, especially when a screw bone must be fixed in a bone of a patient.

BACKGROUND

FIG. 1D illustrates a known ratchet mechanism for a quick connector. The pin 851 has ridges 859 formed on the exterior. The connector 841 has latches 849 capable of latching with the ridges 859 allowing the pins 851 to be inserted into the connector 841 but preventing removal of the pin 851.

For example, a Gamma™ nail system is known that has an operative technique to repair fractures in a femur, a femoral neck and the like. An x-ray template or goniometer is used to pre-operatively plan the insertion of a nail into a cavity formed in the femur. This procedure reams the femur, extends the nail into the reamed cavity in the femur, and then the nail is used with a targeting device and a wire to drill a hole into the femoral neck that precisely locates a lag screw through a hole in the nail at an angle that extends through the femoral neck and into the femoral head. The position of the lag screw must be either central or in the lower half of the femoral head in the frontal plane and on the midline in the lateral plane. The depth of the lag screw is determined from a measurement of the depth of a guide wire inserted into the femoral head through the nail to a depth observed by x-rays. This procedure requires many steps to form the hole and to insert and fix the lag screw, which make the procedure time consuming and difficult to accomplish successfully even for a skilled surgeon who has performed many operations using the procedure.

The Mitek Milagro™ Interference Screw may be used for attachment of soft tissue grafts or bone-tendon-bone grafts to the tibia and/or femur during cruciate ligament reconstruction procedures. This interference screw contains Bioacryl Rapide™ that combines osteoconductive TriCalcium phosphate and a faster, resorbing polymer. This screw has the ability to absorb and enhance bone growth.

Other procedures are known that use multiple lag screws for fixation, which increases the difficulty of these procedures and increases the chances of an error and damaging or fracturing of the femoral head or neck of the patient. One system, the Oasys™ System of Stryker® is a system for repairing fractures of the occipito-cervico-thoracic spine are modular, improving the flexibility in use of the system, the system remains complex with many parts that need to be individually placed and tightened using threads that may loosen over time.

There is a long standing unresolved need for efficient and effective methods and devices for use in emergency and elective surgeries to repair and replace damaged bones and joints.

SUMMARY OF THE INVENTION

A system of orthopedic repair and joint replacement reduces the number of steps required for completing a procedure and provides a device that may be implanted remotely. A remote operation allows active use of x-ray radiation during reaming and/or drilling operations and placement of the first portion of a two-part, orthopedic screw.

By using the two-part screw, a single screw may be adjusted for length without requiring selection of a screw of specific length, reducing the inventory of screws needed in an operating theatre. Also, the two-part screw allows precise positioning of the screw and precise application of compression to a fracture, improving the rate of healing of the fracture.

For example, a screw and retainer system has been developed that reduces the number and improves the outcome for patients requiring repair of fractures in bones. In one example, a two-part screw has two portions. A first portion has a thread for engaging cancellous bone within a portion of a bone on one side of a fracture. The second portion is capable of mating with the first portion and is coupled to a retention mechanism that couples a portion of the bone on the opposite side of the fracture to the portion of bone having the first portion of the screw threaded therein. By tightening the second portion, compression may be exerted that closes the fracture, applies compression across the fracture and improves the rate of healing of the fracture.

One advantage of the system for orthopedic repair and joint replacement is that the two-part screw is capable of joining fractured pieces of a bone across a fracture line without the need of more complex surgical procedures, requiring insertion of multiple pins, large medial nails and multiple retainers. Another advantage of the system is that a femoral head may be shaved and capped without replacement of the femoral head, even with fractures in the femoral head or femoral neck, which might otherwise require removal of the femoral head and neck and replacement by an artificial prosthesis fixed within the femur. Yet other advantages of the system exist as will be apparent to a person of ordinary skill in the art from the examples provided in the detailed description.

BRIEF DESCRIPTION OF THE FIGURES

The drawings show examples of the present invention, which is not limited to the specific examples as represented in the drawings.

FIGS. 1A and 1B illustrate an example of a two-part orthopedic screw.

FIG. 1C depicts an example of a fixation device.

FIG. 1D illustrates a prior art device having a ratchet mechanism in a connector for quick connect to a pin having external ridges.

FIG. 3 illustrates another example of a two-part screw for use with various fixation devices.

FIG. 5 shows another example of a fixing device.

FIGS. 7A-F depict examples of extending members being interconnected.

FIGS. 9A-9E illustrate other examples.

DETAILED DESCRIPTION

Figure 2:
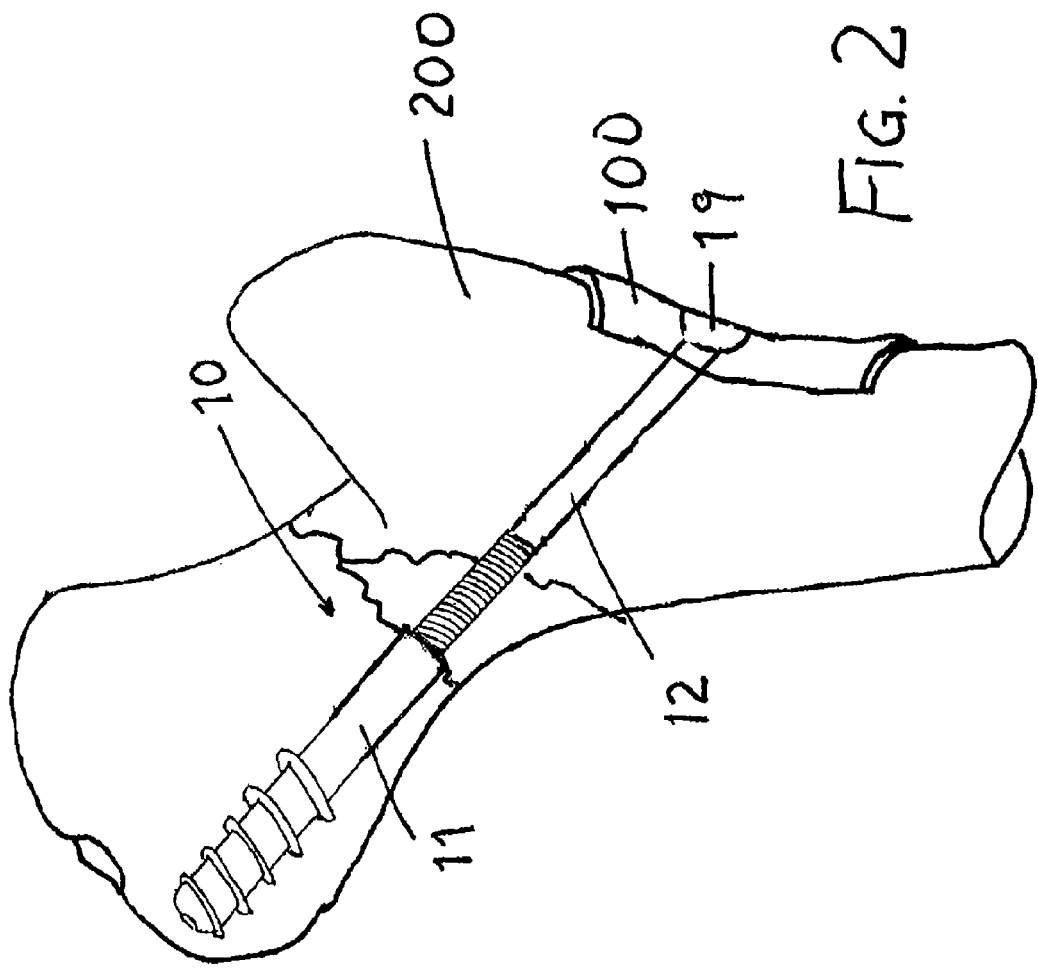
FIG. 2 illustrates, schematically, use of an orthopedic screw to repair a fracture.

The examples described and drawings rendered are illustrative and are not to be read as limiting the scope of the invention as it is defined by the appended claims.

In FIG. 1A, an example of a two-part, orthopedic screw 10 comprises a first portion 11 and a second portion 12 that is capable of being coupled to the first portion, such as by threading a coupling portion 16. Alternatively, the coupling mechanism of the coupling portion 16 may be a one way latching mechanism such as used in plastic zip strips (also referred to as cable ties) or any other coupling mechanism, which has the advantage of locking the second portion 12 in the first portion. A locking or latching mechanism may be incorporated with a threaded coupling mechanism, such as a lock tight adhesive, a retaining pin, or any other mechanism for fixing the coupling portion 16, when it is located in its final position. The second portion 12 is coupled at an opposite end 18 with a cap 19 in the example shown in FIG. 1A. In the example shown in FIG. 1A, the cap 19 resembles a nail head. Any coupling mechanism may be used at this opposite end 18 of the second portion 12. In FIG. 1C, a larger fixing device 100 is shown that has a through hole 101 and a countersunk portion 102, which mates with the cap 19.

Threads 14 are provided on the exterior surface of the first portion 11 for engaging with bone. The threads 14 may be coated with a growth and/or growth factor medium for stimulating bone growth to the threads 14. In FIG. 1B, a cross sectional view of an example of a first portion 11 is shown. The drawings are not to scale, and the size difference between the threads in this example is exaggerated for easier explanation. The cross section of the threads shows the threads progressing from larger to smaller with distance along the first portion 11. For example, it is clear that the first thread 115 is smaller than the next thread 114, which is smaller than the subsequent threads 113, 112 and 111. In actuality, these threads 111-115 are all connected and the width of the threads becomes progressively wider as the threads extend further from the tip 118 of the first portion 111. At some point, in one example, the width of these threads 111-115 may reach a maximum and will remain constant or the width may be constant for all of the threads 111-115. Although the shaft 119 is shown at a constant outer diameter, the shaft 119 may also increase in diameter slightly from the tip 118. FIG. 1B shows that the shaft 119 is tubular, which allows the second portion 12, such as shown in FIG. 1A, to mate with the first portion 11. As an alternative example, the shaft 119 may be a solid rod or a shaft that mates into a tubular section of the second portion 12, reversing the mating shown in FIG. 1A. However, it is preferred to have a smaller outer diameter for the second portion 12 to reduce the complexity of positioning of the second portion 12 in the first portion 11. Therefore, the example of FIG. 1A is a preferred embodiment. In the examples shown in FIGS. 1A and 3, the second portion 12 has a tip 17 that has a reduced diameter for alignment of the tip 17 in the opening 117 of the first portion 11. The inner shaft of the first portion 11 may be threaded 316 and/or may comprise a latch 849 or latches providing coupling by a ratchet mechanism for quick connection.

The purpose of the fixing device 100 in FIG. 1C is to distribute the stresses imposed on the bone 200 across a larger surface area of the bone, as shown in FIG. 2. The advantage of distributing stresses over a larger surface area is a reduction in the incidence of fractures or other damage to the bone by the cap 19. The procedure for introducing the two-part screw 10 into a bone includes drilling a tap hole at a desired location in the bone, inserting the first portion in the tap hole (with or without a guide wire), selecting a fixing device 100 of the appropriate size, shape and type, inserting the second portion 12 through the fixing device 100, and coupling the second portion 12 with the first portion 11. A step may be included to fix the second portion 12 in the first portion 11 to prevent any further rotation of the screw. Also, the second portion 12 may be tightened to apply compression to a fracture located between the first portion 11 and the second portion 12. This may be done with or without the prior application of a cement or bone growth stimulating substance within the fracture, itself.

In FIG. 3, another example of a two-part screw is shown, having a first portion 315 with threading shown schematically and a second portion 16 with threading, in an opposite direction from the threading of first portion 315, shown schematically. The second portion 16 has a fixed cap 319 including an opening 320 that fits a tightening device, such as a torx head or hex key, for example. The tip 17 provides for easy insertion into the first portion 315.

Figure 4:
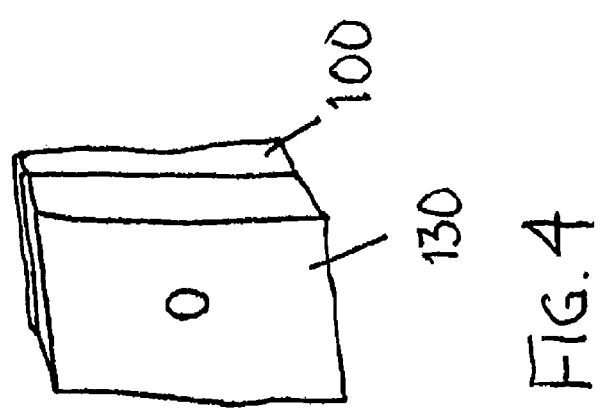
FIG. 4 illustrates a cross sectional view of an example of a fixing device for use with the two-part screw of FIG. 3.

In another example, the fixing device 100 may have a deformable foam inner layer 130, such as illustrated in FIG. 4, which deforms under pressure to distribute the load over a comparatively large area of a bone. For example, the foam layer 130 may be a titanium foam that is bio-compatible or any other type of deformable foam. Alternatively, the entire fixing device may be of a deformable material that takes the shape of the bone, such as an elastomeric material, a plastically deformable material or a visco-elastic, superplastic material. Any material may be used that distributes load over a comparatively large surface of the bone, reducing the chances of breaking, crushing or damaging the bone during fixation of a bone fracture compared to use of a material that does not distribute loads on the surface of the bone. In yet another example, the fixing device 100 may be rigid and may be designed for use on a specific location of a bone. In examples where the fixing device 100 is separate from the screw, various sizes, shapes and types of fixing devices 100 may be provided for use with a single two-part, orthopedic screw 10.

The fixing device 100 may be joined or fixed on the end of the second portion 12 of the screw 10. In this example, a deformable fixing device is more practical than a rigid fixing device, which might require a large number of second portions with differing shapes, sizes and/or types of fixing devices. Nevertheless, the claims are not limited to a specific fixing device.

In FIG. 5A, an example of a fixing device 510 provides for attachment to a plurality of first portions 11 by insertion of second portion 12 through a plurality of holes 512 formed in the fixing device 510. In this example, the first portion 11 is joined to the second portion 12 by ridges 520 of a latching mechanism, which are shown schematically. The ridges 520 engage onto latches (not shown) in the first portion 11 which provides a ratchet mechanism, allowing insertion but not removal. Removal may be provided by a lost 575 or hole that extends into the first portion 11, allowing a latch mechanism to be disengaged, for example. The slot 575 or slots may be used as a retaining lock for a keyed retainer, if removal of the second part from the first part 11 is not required. Thus, the second portion readily press fit into the first portion 11 to any desired depth. The cap 19 may be countersunk flush with the surface of the fixing device 510 as shown in FIG. 5A. In this example, the second portion is attached at one end.

FIG. 5A illustrates an embedded screw 11 having external threads 14 along the exterior surface of embedded screw 11, and a retaining device 510 is illustrated in FIG. 5F. The retaining device 510 may include a plate of any shape made of materials such as a metal or biocompatible polymer. The retaining device 510 may have one or more holes 513, which may be through holes. Counter-sinking 512 may allow a cap 19 to fit flush with the surface of the retaining device 510. A pin 12 is shown having ridges 520 for mating with a ratchet mechanism (not shown) in the embedded screw 11. Alternatively, the surface of the pin 12 may be threaded; however, a ratchet mechanism reduces the time for coupling a plate 510 to one or more embedded screws 11, and a ratchet mechanism reduces costs and complexity of parts, while preventing loosening by unthreading of the retention mechanism 12 from the embedded screw 11. Furthermore, use of a ratchet mechanism allows an embedded screw 11 to be inserted hours, days, or even weeks prior to connecting a retention mechanism 12 to the embedded screw 11, and the retention mechanism 12 may be easily inserted at a later time. A small incision may be made that allows passage of a tightening device, similar to a rivet gun, which allows inserting and tightening of the retention mechanism 12 in an embedded screw 11. In one procedure, one or more embedded screws 11 are inserted into a bone of a patient, and the screws have both a threaded inner surface 316 and latches 849, such as shown in FIG. 1B. The embedded screw 11 has a bone growth medium either integrally combined or applied on the surface, which may include a bone growth stimulating factor. Any loosening of a retaining device 510, such as due to loosening of a conventional screw or a threaded pin 16, in an embedded screw 11, may be corrected by minimally invasive insertion of a retention mechanism 12 into the pre-implanted embedded screw 11 after a bond is established between the pre-implanted embedded screw 11 and the bone, for example. Temporary fixation may use threaded connectors, while permanent connections using the ratchet mechanism. Alternatively, channels 575 may be provided for removing a pin 12 from a screw 11, using a wire or probe.

In FIG. 5B, the retaining devices has holes 531, and a latching mechanism 520 passing through at least one of the holes into a channel (not shown) in the first portion.

In FIG. 5C, the retaining device may additionally include a hook mechanism comprising a coupling mechanism 560 for coupling to the retaining device and a hook 560 extending from the coupling mechanism.

In FIG. 5C-5E illustrate some additional fixation devices, which may be used with an embedded screw 11. FIG. 5B illustrates a plate 530 having a plurality of holes 531 extending into the plate 530. An extension 520 from the opposite surface of the plate is capable of coupling with the embedded screw 11. Thus, the plate 530 provides a plurality of holes 531 for attachment of one or more fixation devices, such as shown in FIG. 5C. In FIG. 5C, a hook 562 is coupled at one end 560 to a ring 564. The ring 564 may have keyways 574, such as shown in FIG. 5D, for example. The keyways 574 may be aligned with keywaves 575 in the embedded screw 11, such as shown in FIG. 5A. A bushing 566, which may be of a flexible or rigid material, may have a key 576 capable of interlocking with keyways 574, 575. Using a screw 568 or a pin 12, a hook 562 may be oriented with respect to the embedded screw 11 in one of a plurality of directions. Hooks 562 may be used to retain other structures and may be open, as shown in FIG. 5C, or may provide a closed loop or channel for guiding or securing other structures.

Figure 6C:
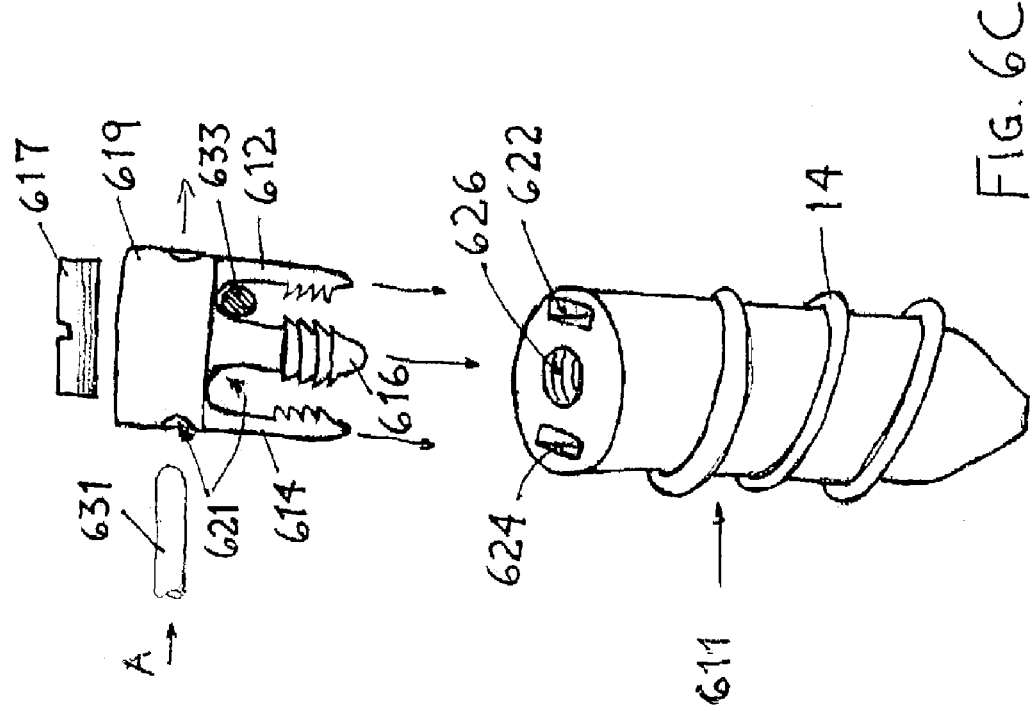
FIGS. 6A-E illustrate examples of fixing device having extending members.
Figure 6A:
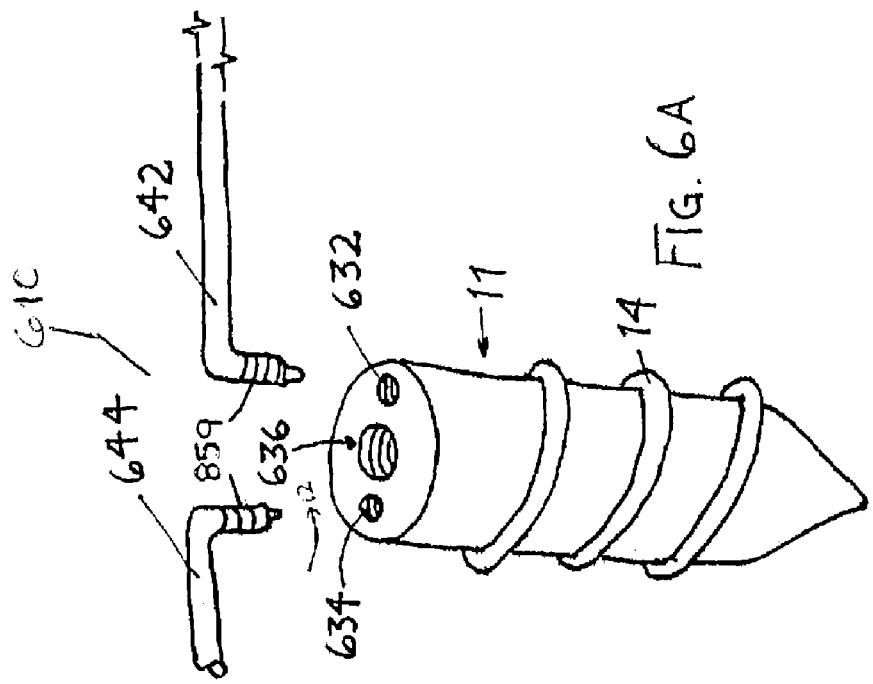

In FIG. 6A, the fixing device 610 includes two extensions 642, and 644, which each have ridges 859 on a portion angled for attachment to the screw 11 in channels 632, 634. A channel 636 is disposed between the two channels 632, 634. In FIG. 6C, a first extension 614, a central extension 616, and a second extension 612 extend from a cap 619. These three extensions 616, 614, 612 couple with channels 622, 624 and 626 of screw 611. In this example, two of the channels, 622 and 624 have a non-round cross section; however, extensions of circular cross section may be used for the screw 11 shown in FIG. 6A. In this example, the device further includes a locking mechanism or nut 617 having an external thread for mating with a locking hole (not depicted) in the cap. The locking nut 617 is capable of securing a cross member 631, 633 or an extension member in one of the plurality of channels 621, which may be closed or partially open.

In order to further stabilize the bone, for example, an extending member 631 may be inserted A through a channel 621 of the cap 619. A locking nut 617 may be screwed into a cavity of the cap 619 to lock the member 631 in place. Another locking nut (not shown) may be inserted to lock another extension member 633 in place provided the cap 619 is secured to the screw 611 and the locking nut extends through a hole above the member 633.

Figure 6E:
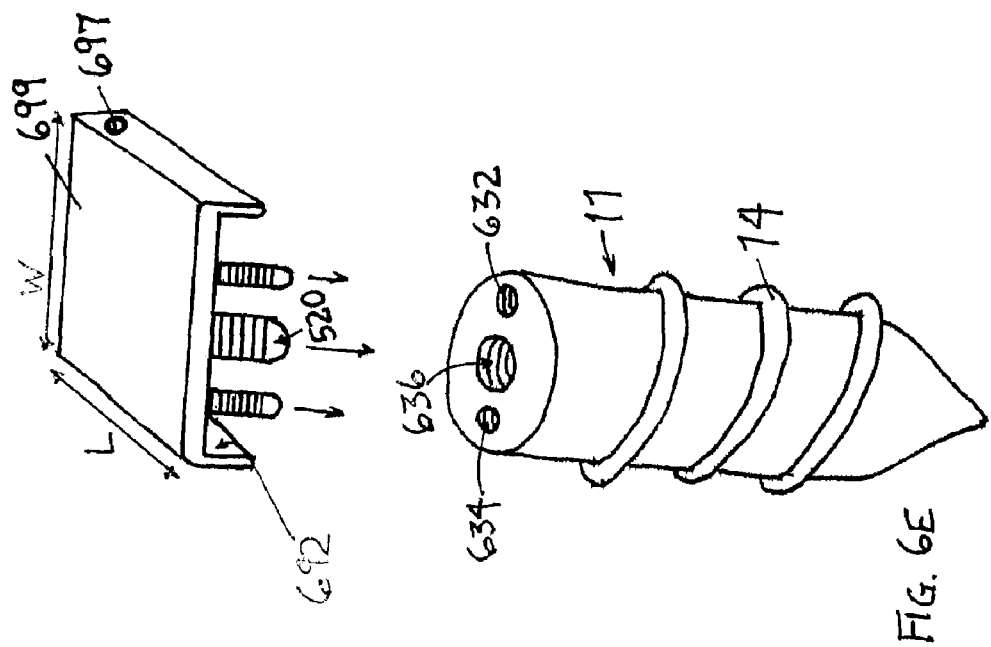
Figure 6B:
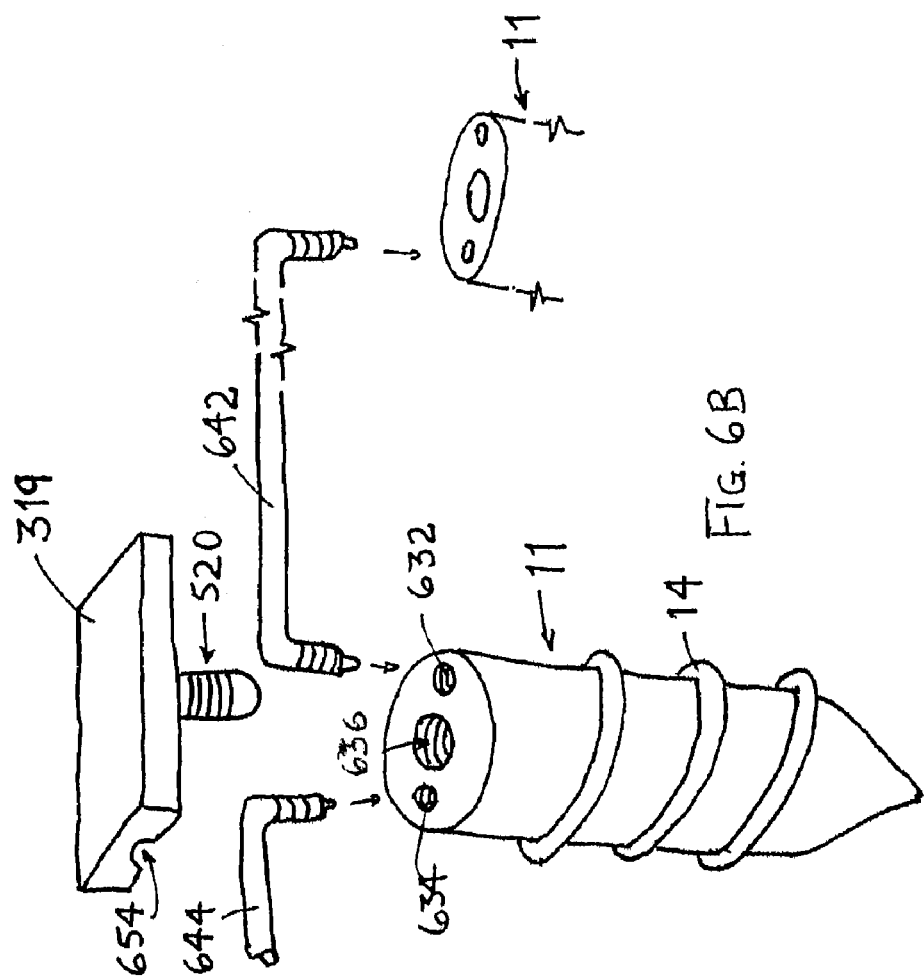

In FIG. 6B, as shown with the screw 11 of FIG. 6A, an extensions 642 assists in attachment of a first screw 11 to a second screw 11. In addition, a plate 319 includes a pin 520, having ridges that engage a latching mechanism in central channel 636. A groove 654 in the underside of the plate 319 may extend through the pin 520 and may be capable of securing extension members 642, 644, 631, 633, 754 to the screw 11 to prevent translation and/or rotation of the extension members 642, 644, 631, 633, 745.

In FIG. 6E, the plate 699 may be an integrated modular unit having a plurality of extensions which may be pins 520. The extensions of FIG. 6E latch with corresponding channels 634, 636, and 632 of the first portion 11 preventing rotation and translation of the plate 699. The plate may have one or more ribs 692 extending from a surface of the plate 699, providing additional stiffening for a plate 699 having a longer length L than width W. In FIG. 6 the plate is shown in perspective view, and the length L is longer than it appears in the drawing. A channel 697 is shown extending through one rib, which may be used to retain an extension member 631, 633, 745 as a cross member.

Figure 6D:
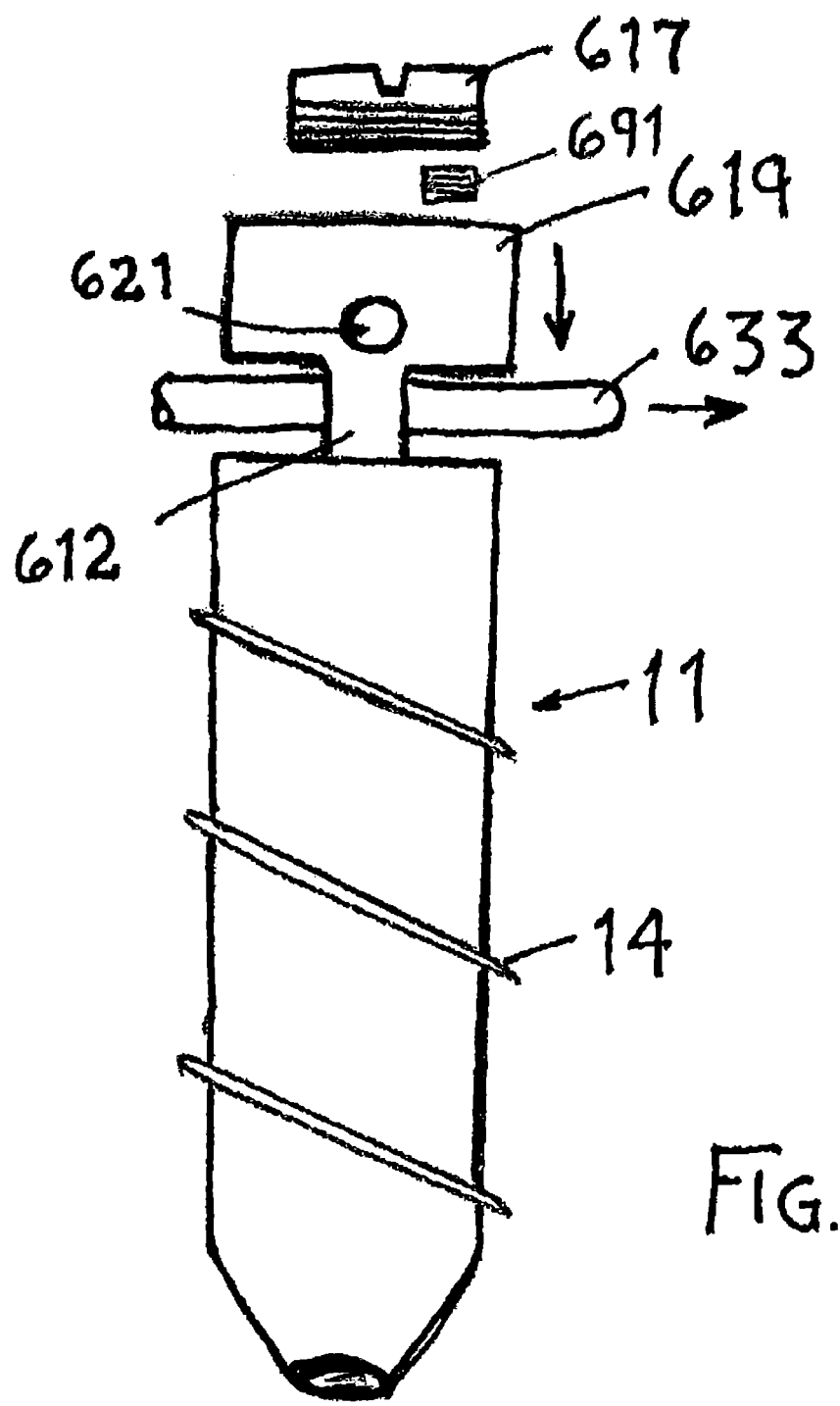

In FIG. 6D, a side view of a cap 619 is shown with a locking nut 691 capable of retaining an extending member 633 inserted in the channel 621 provided on the underside of the cap 619. The locking nut 691 is threaded in a hole through the bottom of the cap 619, and its use is optional.

Figure 7F:
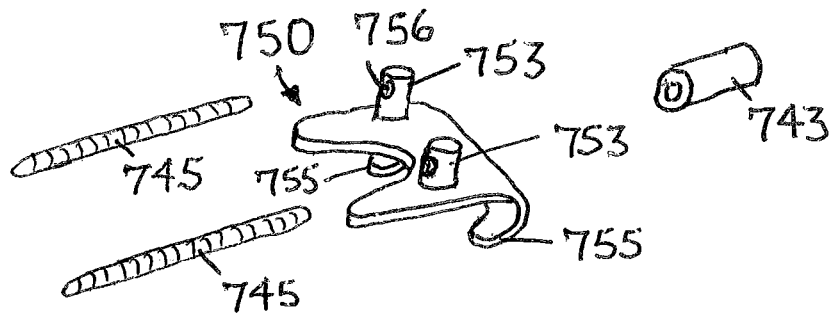
Figure 8A:
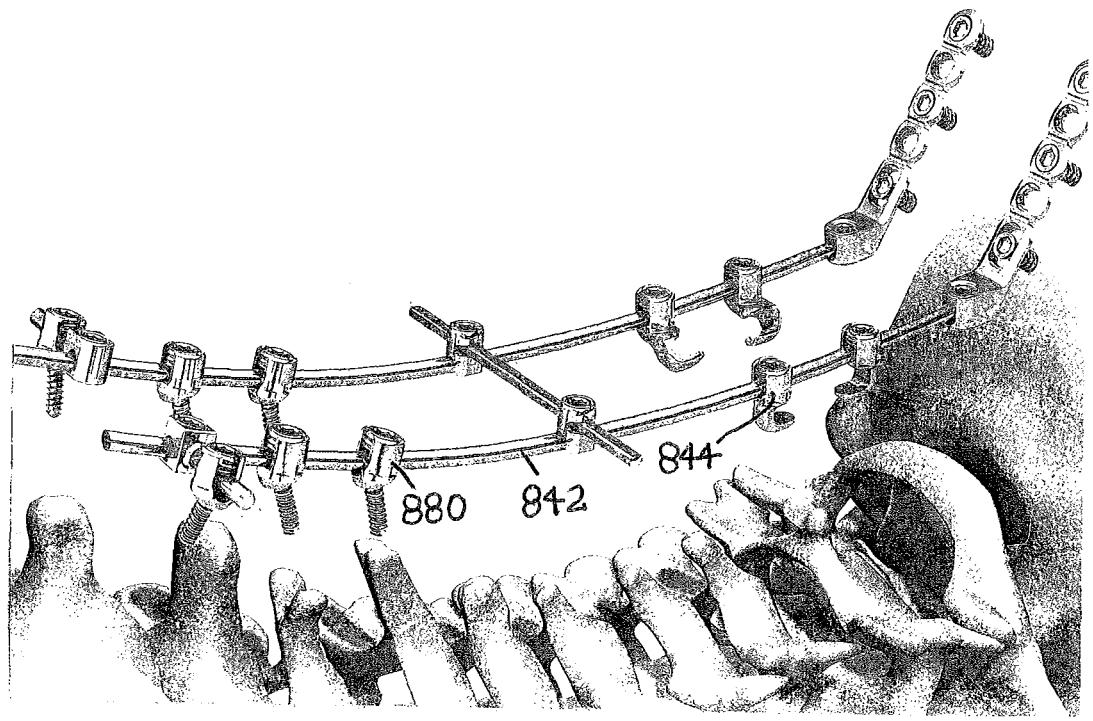
FIG. 8A illustrates a prior art fixing device.

FIGS. 7A-7F illustrate a system having a greater flexibility in design and use than known systems, such as shown in FIG. 8A. Using one or more embedded screws 11, a plurality of retaining devices 742 and/or extensions 745 may be quickly coupled to a bone or bones in a patient. A sleeve 743 may be used to couple one end of a retaining device 742 or extension 745 to another retaining device 742 an extension 745, a cross bar 741 or to other devices. An extension is illustrated in 7D. One device 744 is shown in FIG. 7C mounted on a retaining device 742. Ridges may extend along the entire surface of a retaining device, such as shown in FIGS. 7C and 7D or only along a portion, as shown in FIG. 7B. FIG. 7D illustrates an extension 745 that may be coupled to a retaining device 742, such as by a sleeve 743 providing for, extending the length of a retaining device 742. Furthermore, if properly sized, an extension member 745 may be used to retain a device, such as the one shown in FIG. 7E, between two sleeves 743. As illustrated in 7E, a hook 745 may be pivotally attached 701 by a pivot coupling 747 to a coupling mechanism 744. The coupling mechanism 744 may have a through hole 746 with or without threading or any other coupling mechanism for coupling with a retaining device 742 or extension 745. For example, a pair of sleeves 743 may be used to retain a hook 745 on a portion of an extension 745.

In FIG. 7F, a coupling plate 750 is shaped to fit a vertebrae, providing two hooks 755 joined to two connecting studs 753, each having a channel 756 for coupling with extensions 745 or retaining devices 742. Sleeves 743 may be used to apply compression between hooks 755 and a pair of imbedded screws 11, for example. In one example, a fractured vertebrae is repaired by using four embedded screws 11 for retaining devices 742 attached to each of the screws embedded in locations in the spine. Two vertebrae plates 750 are coupled to the four retaining devices 742 by passing extensions 745 through each of the connecting members 756. A plurality of sleeves 743 are used to couple two extensions 745 to the four retaining devices 742, for example. Compression is applied to the fracture using the ratchet mechanism in the sleeve 743. The retaining devices 742, 642, 644, 745 may be coupled to any fixture, such as the screw 11. The design allows other devices to be integrated at the end of the retaining device 642, 742 or by a hook 745, a cap, a channel or otherwise. Thus, a system using embedded screws 11 may be very flexible in design and rapid to assemble.

In FIG. 7B, the sleeve member 743 includes a channel 797 disposed between the first end and second of the sleeve. In one example, the channel 797 may serve as a passageway for a cross member 741, an extension 745, or a retaining device 742.

In FIGS. 7C and 7E, the ends of the retaining device 742 include ridges capable of being engaged by a latch of a ratchet mechanism. Thus, assembly of a complicated retaining structure may be quire rapid compared to conventional devices. In one example, HDPE is used for extensions which costs much less than the metal systems known in the art and provides some flexibility in the case of thin retaining devices 742.

In FIG. 7F, extensions 745 are coupled to a plate 750. The plate 750 has a shape accommodating the shape of a vertebrae and includes two hooks 755 extending from an edge of the plate. Each of the two hooks is capable of engaging a portion of a vertebrae of a patient, allowing repair of a fracture.

Figure 8B:
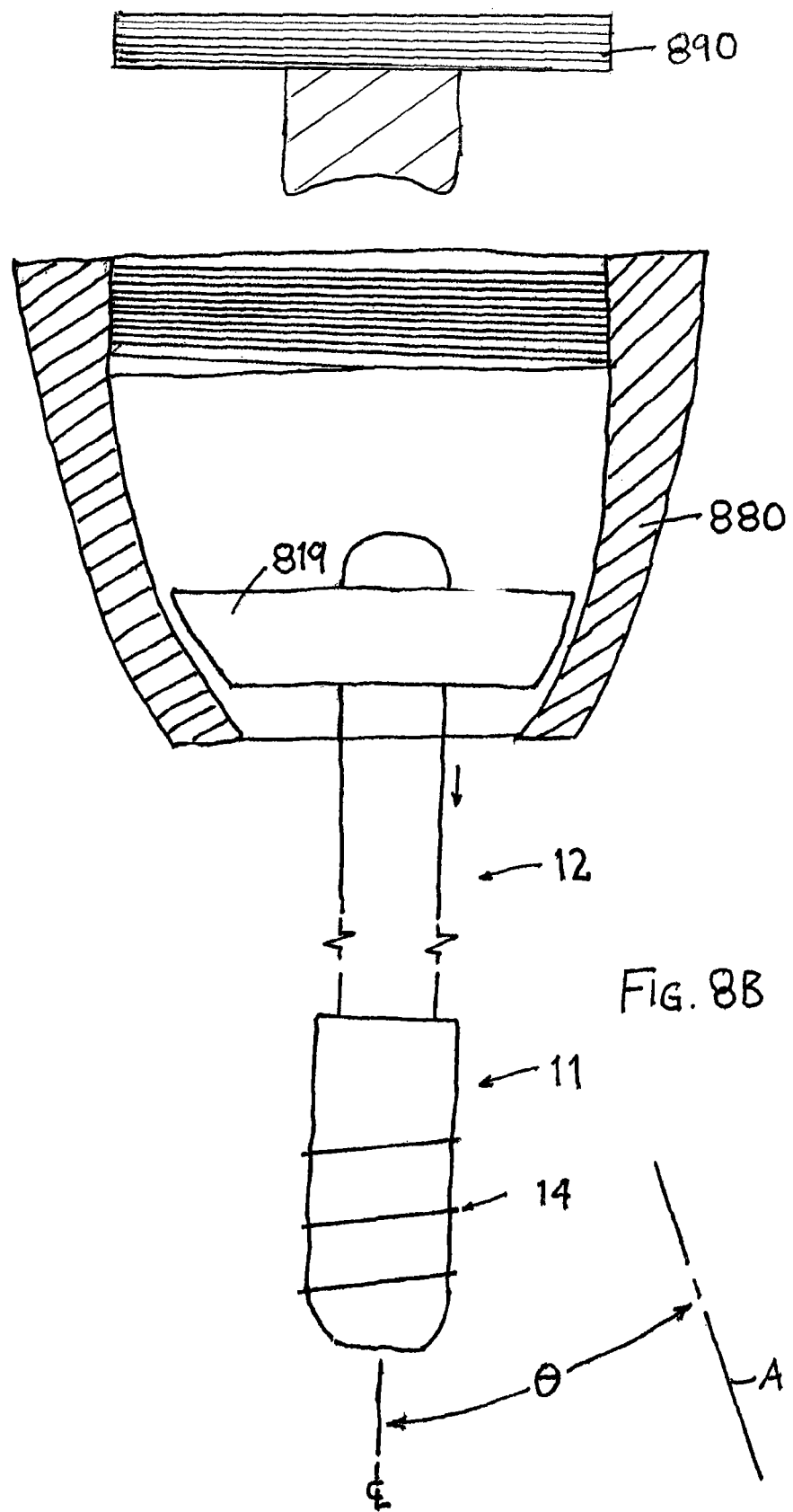
FIG. 8B shows an example of the two-part screw used with a retaining mechanism similar to the device in FIG. 8A.

Polyaxial screws 880 are shown being supported on a rod 842, which may be titanium, for example, in FIG. 8A. In FIG. 8B, a pin 12 includes a cap 819. The pin 12 is coupled to a screw 11. The pin 12 may interconnect with another screw, such as polyaxial screw 880. The system is able to be adjusted or tightened at an angle θ. In one example, a pin 12 has a round head capable of being retained in shell 880 without use of a separate cap 819, reducing the number of parts and chance of failure.

Figure 8C:
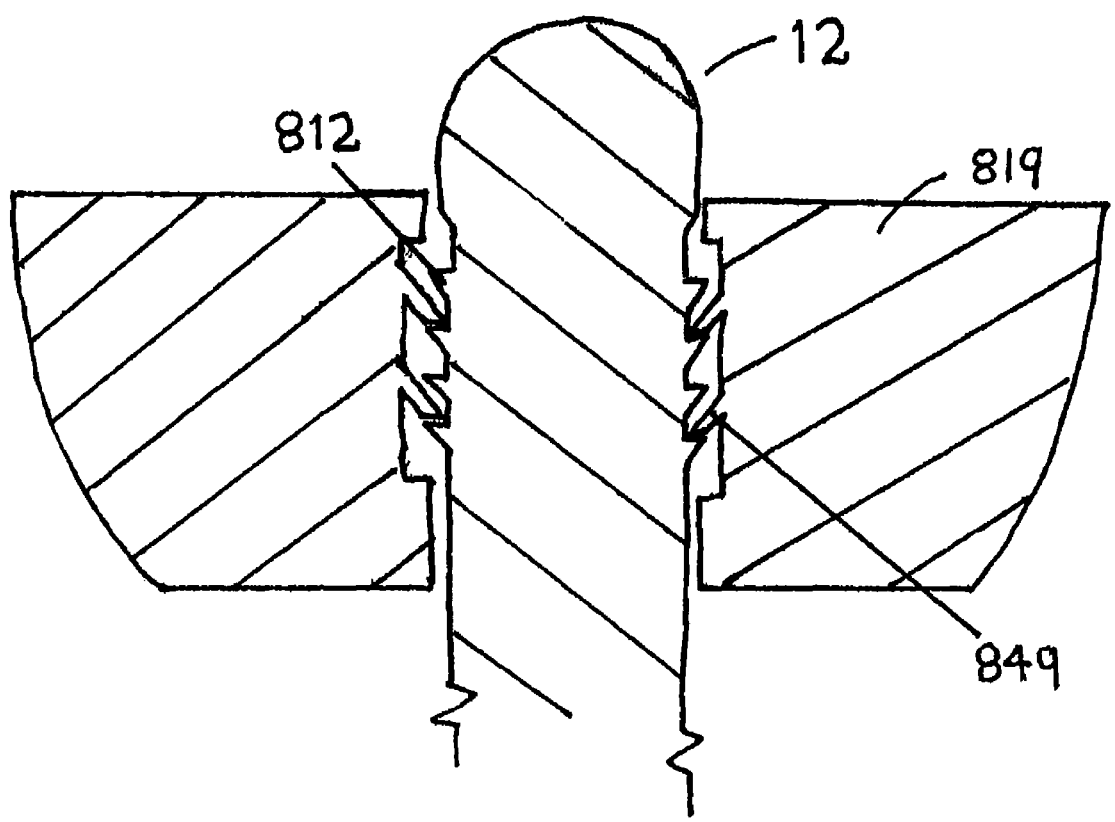
FIG. 8C depicts an example of a second portion of the two part screw being coupled to a cap.

The retaining device includes a hollow head having a body with a cavity formed in the body. An opening is located on one end of the cavity capable of accommodating a locking member 890, and a hole is located on an opposite end of the cavity. The cap 819 has a shape selected to be accommodated pivotally within the cavity. In FIG. 8C, the cap is coupled using a plurality of latches comprising a ratchet mechanism of engaging external ridges 812, 859 extending along a length of a pin 12, 851 opposite to an end having the coupling mechanism for coupling to the first portion 11. The ridges may be shaped to be unidirectional 812 or bidirectional 859.

A two-part screw may be utilized in many parts of the body such as the tibia, femur, humerus, hand or spine.

The screws may be made of any suitable material for use in bones and joints. In one example, a screw may be made of the same materials a Depuy Mitek Milagro™ Interference Screw.

FIG. 9A shows a mechanism for preventing rotation of an embedded screw 10 located in a femoral head. The mechanism uses wires 12 inserted through the shaft of the embedded screw 10, such as shown in FIGS. 9B-9E and the portion cut-away in 9A, which shows the wires extending along the shaft embedded screw 10. In FIG. 9B a central hole 2 is included for use in the procedure that first inserts a wire into the femoral head that is used to guide a drill bit and the self tapping screw 10. In FIG. 9C, the wire tips are shown exiting from between two threads 14. In FIG. 9D a channel 16 extends down the shaft of the screw 10 and is shown bending to an opening 18 from which the wire 12 extends. In FIG. 9E, the channel 16 is arranged to extend through a thread 14. Wires may be inserted into position using push rods, which may be a blunt wire of the same gauge.

Figure 10:
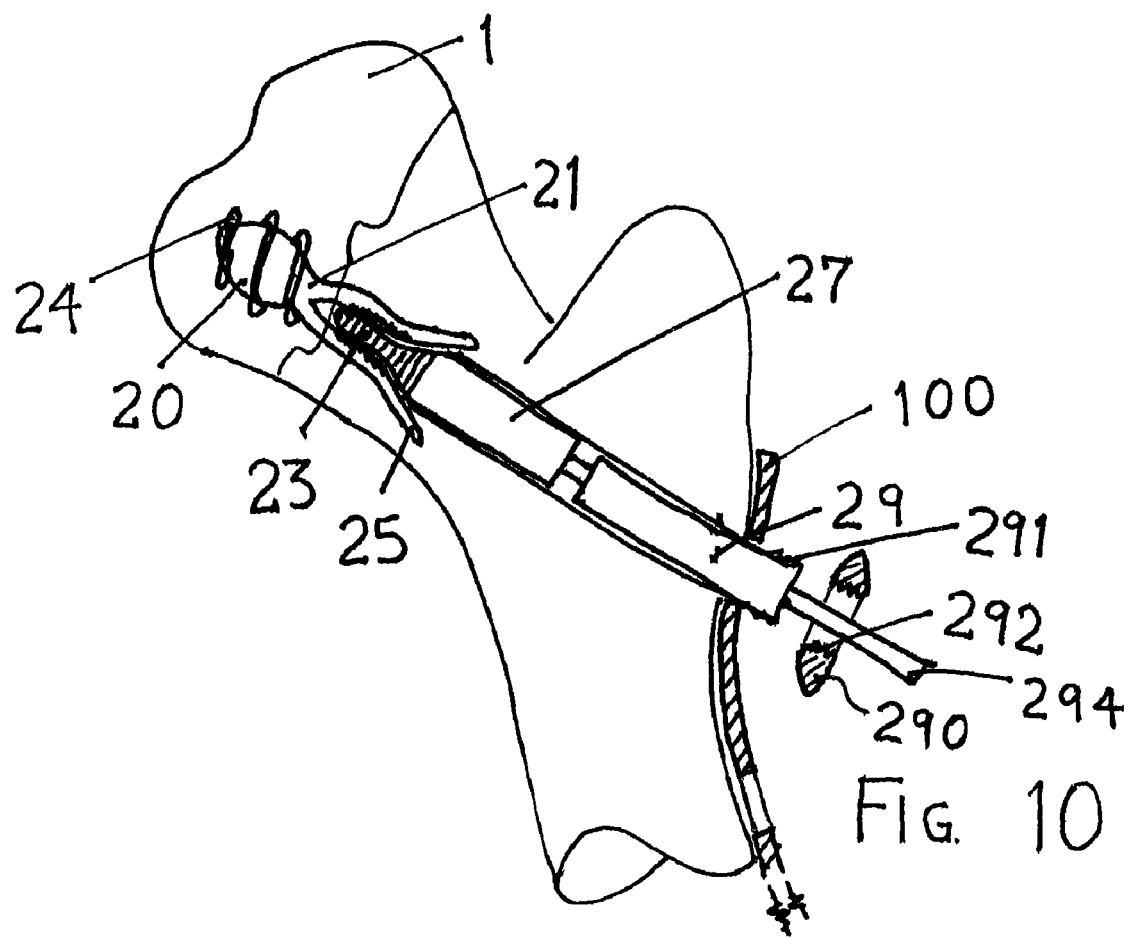
FIG. 10 illustrates yet another example

In FIG. 10, a first portion of a multi-part screw assembly is shown. Embedded screw 20 includes a rounded head with external heads 24, a neck 21 and arms 25. The embedded screw 20 may be threaded into the patients bone, as previously described with reference to FIG. 9A. A person of ordinary skill in the art will understand that other methods may be used, depending on the location of a fracture and the type of bone to be repaired. A second portion 27 is inserted into arms 25, which causes the arms 25 to spread, locking the embedded screw 20 within the bone 1. The spreading arms 25 also apply a slight compression to any fracture between threads 24 and the arms 25. Furthermore, the second portion 27 may be coupled to a third portion 29, which may be a component of a fixation device 100, which may allow additional compression of the fracture in the bone 1. A cap 290 may include a ratchet mechanism or threading on the interior surface 292, capable of mating with the external surface 291 of the third portion 29.

Figure 11A:
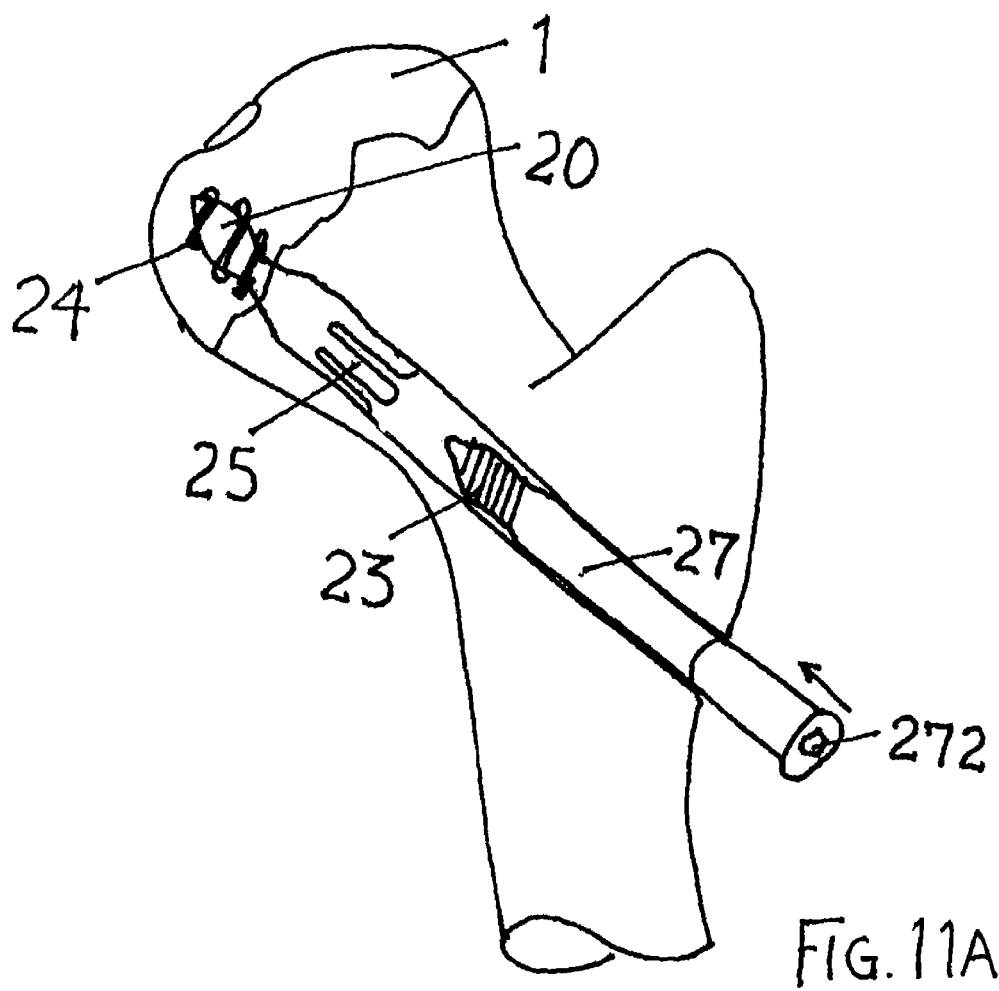
FIGS. 11A-B illustrate other examples
Figure 11B:
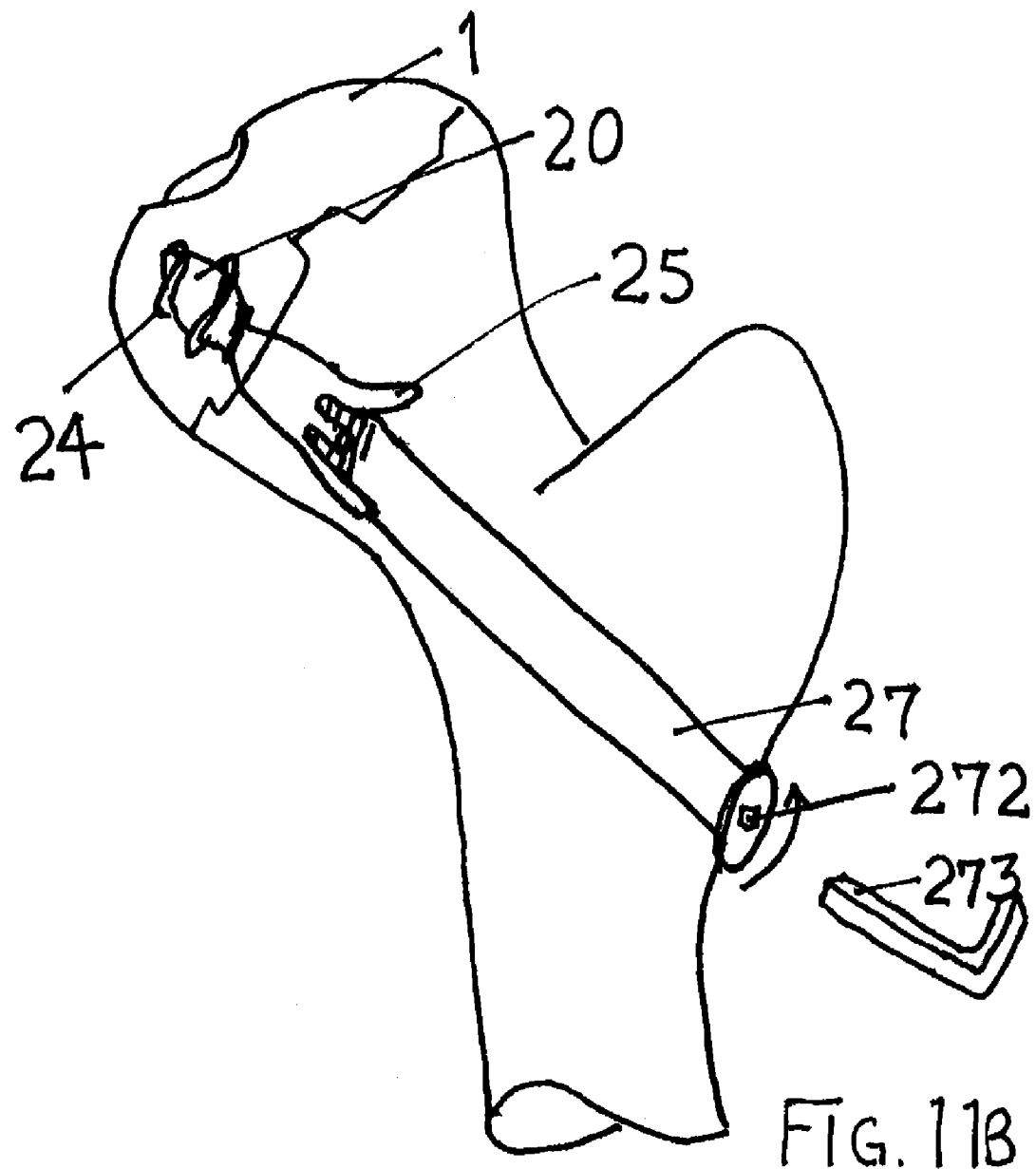

FIG. 11A shows an alternative embodiment of the device disclosed in FIG. 10. In this embodiment, the second portion has a bulbous head 23 and a shaft 27 which mates with and expands the arms 25 of the embedded screw 20. The second portion 27, is shown having a cavity 272 shaped to accept a hex-key or a torques head for threading of the bulbous head 23 into the sheath provided by the arms 25. For example, a hex-key 273 is shown for use in tightening the second portion 27 in FIG. 11B. However, any mechanism may be used for tightening of the second portion 27 in the embedded screw 20. Expansion of one of the arms 25 is illustrated in FIG. 11B. Arms 25 expanding into soft bone and cancellous bone may expand more than other arms 25 without causing the screw to fail. The bulbous head 20 is capable of compacting cancellous bone within the femoral head 1. The neck region 21 may be located at the fracture in the bone 1. Thus, using bone growth factor or bone growth medium, bone growth may be stimulated to grow around the head and neck regions 20, 21. The compression provided by the expanding arms 25 or tightening of the second portion 27 during implantation of the surgical device or thereafter may be used to accelerate healing of the fracture in the bone 1 by closing the fracture and compressing the fracture together. In FIGS. 11A-11B, a wire used for guiding the insertion of the embedded screw 20 is removed prior to inserting the second portion of the screw 27. However, the second portion 27 may be cannulated such that the second portion 27 may be fit over the wire, allowing the wire to assist in directing the second portion 27 into the arms 25 of the embedded screw 20.

Alternative combinations and variations of the examples provided will become apparent based on this disclosure. It is not possible to provide specific examples for all of the many possible combinations and variations of the embodiments described, but such combinations and variations may be claims that eventually issue.

What is claimed is:

1. A surgical fixing device for use in a bone of a patient, the bone of the patient not being included as any portion of the device, the device comprising:
 a first portion is an embedded screw having an exterior threaded portion for contacting the bone and threading into the bone, whereby the first portion is capable of being embedded in the bone and secured in contact with the bone by the exterior threaded portion engaging with the bone;

a second portion discrete and separate from the first portion having a coupling mechanism for coupling to the first portion, the second portion being arranged with the first portion, when used for surgical fixing, such that the first portion is embedded entirely within the bone below any exterior surface of the bone, and the second portion extends from the first portion; and a retaining device is coupled by the coupling mechanism of the second portion to the first portion and is arranged, when used for surgical fixing, such that the first portion and the retaining device are capable of applying compression to a fracture in the bone, whereby a portion of the second portion extends between the first portion and the retaining device, adjustably joining the first portion to the retaining device, such that the fracture of the bone is capable of being disposed between the first portion and the retaining device.

2. The device according to claim 1, wherein the first portion is a cannulated screw having self tapping threads and an axial direction along a longitudinal axis of the screw.

3. The device according to claim 2, wherein the threads are coated with a bone growth medium.

4. The device according to claim 2, wherein the first portion comprises at least one channel extending along the axial direction of the screw, and the second portion is connected to the first portion by inserting the second portion into at least one of the at least one channels.

5. The device according to claim 4, wherein the at least one channel includes a ratchet mechanism for coupling with ridges on the exterior of a portion of the second portion.

6. The device according to claim 5, wherein the at least one channel comprises at least three channels.

7. The device according to claim 6, wherein the second portion, comprises three extensions for securing the second portion in the at least three channels.

8. The device according to claim 7, wherein two of the at least three channels have a non-round cross-section.

9. The device according to claim 1, wherein the retaining device is an elongated member attached at one end to the second portion.

10. The device according to claim 7, wherein the second portion extends from a surface of the retaining device, the retaining device comprising a cap having at least one cap channel and at least one extension member capable of being retained within the at least one cap channel.

11. The device according to claim 10, wherein the at least one cap channel comprises a plurality of cap channels capable of retaining a plurality of the at least one extension member.

12. The device according to claim 11, wherein the plurality of cap channels comprises a hole through a body of the cap and a pair of channels formed by the three extensions and the surface of the cap such that at an extension member is capable of being retained between a central one of the three extensions and either of the two of three extensions disposed on either side of the central one of the three extensions.

13. The device of claim 12, further comprising a locking nut having an external thread for mating with a locking hole in the cap, the locking nut being capable of securing an extension member in one the plurality of channels.

14. A surgical method for surgically fixing the device of claim 1 in a bone of a patient comprising:
   boring a hole in the bone of the patient;
   inserting a wire into the hole;
   threading the first portion of the device of claim 1 into the hole by inserting the wire into a channel centered in the first portion such that the first portion is entirely embedded in the bone, wherein the first portion is disposed entirely within the bone and below any exterior surface of the bone; and
   coupling the second portion of the device of claim 1 to the first portion before removing the wire or after removing the wire, and compressing a fracture in the bone disposed between the first portion and the retaining device of the device of claim 1.

15. The method of claim 14, further comprising:
   coupling a hook mechanism to the retaining mechanism such that the hook mechanism engages a portion of the bone, prior to the step of compressing.

\* \* \* \* \*